United States Patent [19]

McCurry, Jr. et al.

[11] Patent Number: 5,430,131
[45] Date of Patent: Jul. 4, 1995

[54] METHOD FOR PREPARING STABILIZED ALKYL GLYCOSIDES

[75] Inventors: Patrick M. McCurry, Jr., Lansdale; Janet R. Varvil, Chalfont, both of Pa.

[73] Assignee: Henkel Corporation, Plymouth Meeting, Pa.

[21] Appl. No.: 257,220

[22] Filed: Jun. 8, 1994

Related U.S. Application Data

[63] Continuation of Ser. No. 918,818, Jul. 22, 1992, abandoned, which is a continuation-in-part of Ser. No. 873,908, Apr. 24, 1992.

[51] Int. Cl.⁶ .................... C07H 1/06; C07H 15/04
[52] U.S. Cl. .................... 536/18.5; 536/18.6; 536/124; 536/127
[58] Field of Search .............. 536/127, 124, 18.5, 536/18.6

[56] References Cited

U.S. PATENT DOCUMENTS

| | | | |
|---|---|---|---|
| 2,235,783 | 3/1941 | White | 536/18.6 |
| 2,356,565 | 8/1944 | Chwala | 536/18.6 |
| 2,390,507 | 12/1945 | Cantor | 536/4.1 |
| 2,422,328 | 6/1947 | Young | 536/4.1 |
| 3,219,656 | 11/1965 | Boettner | 536/18.6 |
| 3,375,243 | 3/1968 | Nevin et al. | 536/18.6 |
| 3,450,690 | 6/1969 | Gibbons et al. | 536/18.5 |
| 3,547,828 | 12/1970 | Mansfield et al. | 252/351 |
| 3,598,865 | 8/1971 | Lew | 536/18.6 |
| 3,640,998 | 2/1972 | Mansfield et al. | 536/18.3 |
| 3,707,535 | 12/1972 | Lew | 536/18.6 |
| 3,721,633 | 3/1973 | Ranauto | 252/527 |
| 3,737,426 | 6/1973 | Throckmorton et al. | 536/111 |
| 3,772,269 | 11/1973 | Lew | 536/4.1 |
| 3,839,318 | 10/1974 | Mansfield | 536/18.6 |
| 3,974,138 | 8/1976 | Lew | 536/18.6 |
| 4,011,389 | 3/1977 | Langdon | 536/4.1 |
| 4,223,129 | 9/1980 | Roth et al. | 536/18.6 |
| 4,472,170 | 9/1984 | Hellyer | 536/18.6 |
| 4,557,729 | 12/1985 | McDaniel, Jr. et al. | 536/124 |
| 4,596,602 | 6/1986 | Bennett | 536/103 |
| 4,762,918 | 8/1988 | McDaniel et al. | 536/124 |
| 4,904,774 | 2/1990 | McDaniel et al. | 536/127 |
| 4,950,743 | 8/1990 | McCurry et al. | 536/18.6 |
| 4,959,468 | 9/1990 | Ravi et al. | 536/127 |
| 5,104,981 | 4/1992 | Yamamuro et al. | 536/127 |
| 5,130,420 | 7/1992 | Yamamuro et al. | 536/124 |
| 5,266,690 | 11/1993 | McCurry et al. | 536/18.6 |

FOREIGN PATENT DOCUMENTS

| | | |
|---|---|---|
| 0387913 | 9/1990 | European Pat. Off. . |
| 0388857 | 9/1990 | European Pat. Off. . |
| WO9119723 | 12/1991 | WIPO . |

Primary Examiner—William H. Beisner
Assistant Examiner—Everett White
Attorney, Agent, or Firm—Wayne C. Jaeschke; John E. Drach; Henry E. Millson, Jr.

[57] ABSTRACT

Glycoside products having a propensity to discolor and/or to exhibit haze under aqueous alkaline or neutral pH conditions can be stabilized to substantially reduce the extent of discoloration and to essentially eliminate any haze which might also be present by adjusting the pH of a hydrogen peroxide-free aqueous solution of the alkyl glycoside product to about 7 prior to treatment with a metal borohydride material which at the end of the reaction period is consumed resulting in a stabilized alkyl polyglycoside product which does not exhibit a haze in an aqueous solution at a pH of about 7.

14 Claims, No Drawings

METHOD FOR PREPARING STABILIZED ALKYL GLYCOSIDES

CROSS-REFERENCE TO RELATED APPLICATIONS

This application is a continuation of application Ser. No. 07/918,818 filed on Jul. 22, 1992, now abandoned, which is a continuation-in-part of Ser. No. 07/873,908 filed on Apr. 24, 1992.

BACKGROUND OF THE INVENTION

1. Field of the Invention

This invention relates to an improved method for preparing stabilized alkyl glycosides by treatment with a metal borohydride after a peroxide bleaching step.

2. Description of the Related Art

Alkyl glycosides are conveniently prepared by reacting an alcohol of the type and chain length which is desired to form the "alkyl" portion of the glycoside of interest with a saccharide reactant (e.g., a monosaccharide such as glucose, xylose, arabinose, galactose, fructose, etc., or a polysaccharide such as starch, hemicellulose, lactose, maltose, melibiose, etc.) or with a glycoside starting material wherein the aglycone portion thereof is different from the alkyl substituent desired for the ultimate alkyl glycoside product of interest. Typically, such reaction is conducted at an elevated temperature and in the presence of an acid catalyst. Various alkyl glycoside products and processes for making same are disclosed in U.S. Pat. No. 2,235,783 (White, issued Mar. 18, 1941); U.S. Pat. No. 2,356,565 (Chwala, issued Aug. 22, 1944); U.S. Pat. No. 2,390,507 (Cantor, issued Dec. 11, 1945); U.S. Pat. No. 2,442,328 (Young, issued Jun. 17, 1947); U.S. Pat. No. 3,219,656 (Boettner, issued Nov. 23, 1965); U.S. Pat. No. 3,375,243 (Nevin et al., issued Mar. 26, 1968); U.S. Pat. No. 3,450,690 (Gibbons et al., issued Jun. 17, 1969); U.S. Pat. No. 3,547,828 (Mansfield et al., issued Dec. 15, 1970) U.S. Pat. No. 3,598,865 (Lew, issued Aug. 10, 1971); U.S. Pat. No. 3,640,998 (Mansfield et al., issued Feb. 8, 1972); U.S. Pat. No. 3,707,535 (Lew, issued Dec. 26, 1972); U.S. Pat. No. 3,721,633 (Ranauto, issued Mar. 20, 1973); U.S. Pat. No. 3,737,426 (Throckmorton et al., issued Jun. 5, 1973); U.S. Pat. No. 3,772,269 (Lew, issued Nov. 13, 1973); U.S. Pat. No. 3,839,318 (Mansfield, issued Oct. 1, 1974); U.S. Pat. No. 3,974,138 (Lew, issued Aug. 10, 1976); U.S. Pat. No. 4,011,389 (Langdon, issued Mar. 8, 1977); and U.S. Pat. No. 4,223,129 (Roth et al., issued Sept. 16, 1980).

In the preparation of alkyl glycoside products, it is not uncommon for such products to develop an undesirably dark coloration during the course of the synthesis and isolation procedures employed. Various procedures have been suggested for improving the color of such dark colored glycoside products including, for example, treatment with bleaching reagents such as hydrogen peroxide; intentional color formation by heat treatment under alkaline conditions followed by removal (e.g., by precipitation, filtration, etc.) of dark colored impurities generated during said treatment procedure; treatment with decolorizing adsorbents such as particulate carbon materials, etc.; and the like. See in this regard, for example, Gibbons' U.S. Pat. No. 3,450,690 which discloses an alkaline heat treatment/separation procedure that can optionally be followed by treatment with bleaching agents such as hydrogen peroxide or by treatment with decolorizing carbons. See also Cantor's U.S. Pat. No. 2,390,507; White's U.S. Pat. No. 2,235,783; Example 1 of Throckmorton et al.'s U.S. Pat. No. 3,737,426; Examples 5 and 10 of Langdon's U.S. Pat. No. 4,011,389; and Example 1 of U.S. Pat. No. 4,472,170 to Hellyer (issued Sept. 18, 1984) for teachings related to the use of carbon adsorbents for the decolorization of various alkyl glycoside products.

Even when glycoside products are originally prepared (or are subsequently decolorized in accordance with one or more of the procedures set forth above) in a fashion which results in initial color characteristics acceptable for certain applications, such products nonetheless commonly exhibit a propensity to discolor (i.e., darken) as a function of time even under relatively mild storage conditions (e.g., at neutral or slightly acidic pH and normal room temperatures, i.e., 20° C.–25° C.). The propensity to discolor is greatly accentuated (i.e., in terms of the intensity and rapidity thereof) by exposure to elevated temperatures (such as, for example, in the range of 40° C. to 100° C. or more) and/or exposure to relatively strong alkaline aqueous environments (i.e., pH of 8 to 12). Generally speaking, the extent of discoloration is related to the severity of the pH/temperature/time to which the glycoside product is exposed. In U.S. Pat. No. 4,557,729 to McDaniel et al. (issued Dec. 10, 1985), the aforementioned problem of color deterioration of glycoside products during storage thereof is discussed and a method for obviating such problem is disclosed which entails first bleaching the glycoside product of interest with an oxidizing agent such as ozone, hydrogen peroxide, hypochlorite, etc., and thereafter exposing the resulting bleached glycoside product to a source of sulfur dioxide (e.g., sulfur dioxide gas, sodium sulfite, sodium metabisulfite, sodium hydrosulfite, etc.) to stabilize said glycoside product against color degradation. While the indicated method has been found to be quite effective in stabilizing the color of glycoside products against deterioration or darkening thereof under relatively mild storage conditions (e.g., at pH's in the range of from about 3 to about 7 and at temperatures in the range of from about 20° C. to about 30° C.), it has also been found to be not nearly as effective (and, in fact, less effective than is desired in many cases) in stabilizing against color deterioration under harsher conditions such as those involving prolonged storage at elevated temperatures (e.g., 35° C. to 60° C. or more) and those involving relatively high pH (e.g., pH=8 or more) environments, even in situations involving relatively short term/low temperature exposure. Accordingly, it would be highly desirable to provide a method for imparting improved high temperature and/or alkaline color stability to glycoside products which are otherwise prone to darken substantially upon exposure to high temperatures and/or alkaline conditions. European patent application 0387913 teaches that a method of producing an alkyl glycoside which is stable in hue and in color which utilizes a metal borohydride decolorization step which comprises treating an aqueous solution of the alkyl glycoside having a pH of about 8.7 to 9.3 with hydrogen peroxide, eliminating the residual hydrogen peroxide through reaction with a metal borohydride and thereafter decomposing the borohydride with acid. European patent application 0388857 teaches a method of producing an alkyl glycoside which is stable in hue and in color which utilizes a metal borohydride decolorization step which comprises reacting a reaction mixture containing an alkyl glycoside and unreacted higher alcohol with metal borohydride. U.S. Pat. No. 4,959,468 teaches a method for improving the color stability of glycoside products which comprises treating the glycoside product by contacting the glycoside product with a color stabilizing amount of from about 0.01 to about 2 weight percent, on a glycoside product dry weight basis, of a borohydride material selected from the group consisting of Group I or Group II metal borohydride salts for a time period sufficient to substantially reduce the propensity of the glycoside product to darken upon exposure to elevated temperatures under alkaline conditions. This method does not eliminate haze which may develop in aqueous solutions of alkyl polyglycoside products having a pH in the 6–8 range. There are no methods in the prior art which improve the color stability of a glycoside product and eliminate haze. It is therefore, an object of the present invention to not only improve the color stability of a glycoside product but also to clarify the glycoside product by substantially eliminating haze which may be exhibited by aqueous solutions of alkyl polyglycoside products having a pH in the 6–8 range.

SUMMARY OF THE INVENTION

It has now been discovered that glycoside products having a propensity to discolor and/or to exhibit haze under aqueous alkaline conditions or at pH in the range of 6–8 and/or upon prolonged exposure to elevated temperatures can be stabilized to substantially reduce the degree or extent of discoloration and to essentially eliminate any haze which might also develop by treating the alkyl glycoside product according to the process of the present invention. The process according to the invention comprises first eliminating haze by adjusting the pH of an aqueous solution of a hydrogen peroxide-free glycoside product to from about 3 to about 8 and maintaining the pH in that range at room temperature or at an elevated temperature for a period of time sufficient to substantially eliminate the haze. After the haze has been eliminated, the pH of the solution is raised to 9–11 and the solution is then treated with a small but effective amount of a metal borohydride material which at the end of the reaction period is consumed resulting in a stabilized alkyl polyglycoside product which does not exhibit a haze in an aqueous solution at a pH of about 7.

DESCRIPTION OF THE PREFERRED EMBODIMENTS

Glycoside products to which the present invention is beneficially applicable include any glycoside materials such as long chain alkyl monoglycosides, long chain alkyl polyglycosides, short chain alkyl mono- and polyglycosides, and the like which are prone to darken or discolor to a significant extent upon prolonged exposure to elevated temperatures and/or upon short or long term exposure to either high or low temperatures or both under neutral or alkaline pH in aqueous solutions.

Generally speaking, glycoside materials to which present invention is applicable include those of the formula I:

(I)

wherein R is a monovalent organic radical containing from about one to about 30 carbon atoms. Examples of such monovalent saturated aliphatic, unsaturated aliphatic or aromatic radicals include but are not limited to alkyl, hydroxyalkyl, alkenyl, hydroxyalkenyl, aryl, alkylaryl, hydroxyalkylaryl, arylalkyl, alkenylaryl, arylalkenyl, and the like. The preferred values of R are monovalent, saturated aliphatic groups which contain from 1 to about 18 carbon atoms and more preferably from 1 to about 16 carbon atoms. R' is a divalent hydrocarbon radical containing from 2 to about 4 carbon atoms; y is a number having an average value of from 0 to about 12. The preferred values of y are from 0 to about 5 with the most preferred being 0. G represents a moiety derived from a reducing saccharide containing 5 or 6 carbon atoms. The preferred reducing saccharides are arabinose, xylose, glucose, galactose and combinations thereof. n is a number having an average value from 1 to about 6 and preferably from 1 to about 3 and most preferably from 1 to about 2.

Glycoside products suitable for treatment in accordance with the present invention also include derivatives of products of the formula I above including, for example, those in which one or more of the normally free (i.e., unreacted) hydroxyl groups of the saccharide moiety, G, have been alkoxylated, preferably, ethoxylated or propoxylated, so as to attach one or more pendant alkoxy or polyalkoxy groups in place thereof. In the case of the indicated alkoxylated derivatives, the amount of alkylene oxide, e.g., ethylene oxide, propylene oxide, employed will generally correspond to from about 1 to about 20 and preferably from about 3 to about 10 moles thereof per mole of saccharide moiety. In regard to the foregoing, it should be noted that pure glycoside products of the formula I above are, generally speaking, color-free or light in color and are prone to neither haze formation nor discoloration upon exposure to aqueous conditions wherein the pH is 7 or above or to elevated temperatures. However, co-products or by-products which are apparently unavoidably generated to one degree or another during the manufacturing process and remain in the product after addition are either dark in color as originally generated, latently prone to darkening upon subsequent exposure to elevated temperatures or to alkaline conditions or upon prolonged storage under even relatively mild storage conditions. In addition, substances added during the manufacturing process can also remain in the product and result in the appearance of a haze or opaqueness. Moreover, even when dark colored reaction products are subjected to oxidative bleaching operations to lighten the color thereof to acceptable levels, the resulting bleached reaction products have been found to still contain materials which can be either residual color-forming species which survive the bleaching operation and/or color-forming species generated during said bleaching operation which are prone to darken substantially upon prolonged storage at elevated temperatures and/or exhibit an unacceptable haze at neutral or alkaline conditions. The propensity to darken substantially under the indicated conditions has been found to persist even after post-bleaching sulfur dioxide treatment of the resulting reaction product in accordance with U.S. Pat. No. 4,557,729.

The process according to the invention is especially adaptable to glycoside products formed by reaction of glucose with an alcohol in the presence of an acid catalyst such as sulfuric acid, para toluenesulfonic acid, or mono- or polyalkylated aryl mono- or polysulfonic acids such as dodecylbenzenesulfonic acid followed by neutralization of the catalyst with a base such as sodium hydroxide, and removal of the excess alcohol, normally by a distillation operation. The distillation residue which contains the glycoside product is first dissolved in water and then subjected to a bleaching operation with such bleaching agents as ozone, hydrogen peroxide and sulfur dioxide, or hydrogen peroxide to yield a decolorized glycoside product. The decolorized product, free of bleaching agents such as hydrogen peroxide, is then color stabilized by treatment with a Group I or Group II metal borohydride material such as sodium borohydride as taught in U.S. Pat. No. 4,959,468, the entire contents of which are incorporated herein by reference. It has been observed that in spite of the Group I or Group II metal borohydride treatment of the glycoside products, aqueous solutions of alkyl polyglycoside products often exhibit a haze at a pH of from 6 to 8, the pH range in which commercial cleaning products are usually formulated. Examples of such commercial cleansing products include hand dishwashing detergents, shampoos, and hand cleansers. These types of products are usually formulated so that they exhibit a pH in the range of from 6 to 8.

Glycoside products to which the process according to the invention is particularly applicable include compositions which are comprised of mixtures of compounds of formula I wherein G represents a moiety derived from a reducing saccharide containing 5 or 6 carbon atoms; y is zero; n is a number from 1 to 3; and R is an alkyl radical having from 6 to 18 carbon atoms in which the average carbon chain length of the alkyl groups of the compounds of formula I in the composition is from about 9 to about 14 and wherein the composition is comprised of a mixture of two or more of at least binary components of alkylpolyglycosides wherein each binary component is present in the mixture in relation to its average carbon chain length in an amount effective to provide the surfactant composition with the average carbon chain length of about 9 to about 14 and wherein at least one, or both binary components, comprise a Flory distribution of polyglycosides derived from an acid-catalyzed reaction of an alcohol containing 6–20 carbon atoms and a suitable saccharide from which excess alcohol has been separated. Such compositions are disclosed in application Ser. No. 07/774,430, filed on Oct. 10, 1991, now abandoned, the entire contents of which are incorporated herein by reference. Other glycoside products to which the process according to the invention is particularly applicable include compositions which are comprised of mixtures of compounds of formula I wherein G represents a moiety derived from a reducing saccharide containing 5 or 6 carbon atoms; y is zero; n is a number from 1.8 to 3; and R is an alkyl radical having from 8 to 20 carbon atoms. The composition is characterized in that it has increased surfactant properties and an HLB in the range of about 10 to about 16 and a non-Flory distribution of glycosides, which is comprised of a mixture of an alkyl monoglycoside and a mixture of alkyl polyglycosides having varying degrees of polymerization of 2 and higher in progressively decreasing amounts, in which the amount by weight of polyglycoside having a degree of polymerization of 2, or mixtures thereof with the polyglycoside having a degree of polymerization of 3, predominate in relation to the amount of monoglycoside, said composition having an average degree of polymerization of about 1.8 to about 3. Such compositions can be prepared by separation of the monoglycoside from the original reaction mixture of alkyl monoglycoside and alkyl polyglycosides after removal of the alcohol. This separation may be carried out by molecular distillation and normally results in the removal of about 70–95% by weight of the alkyl monoglycosides. After removal of the alkyl monoglycosides, the relative distribution of the various components, mono- and poly-glycosides, in the resulting product changes and the concentration in the product of the polyglycosides relative to the monoglycoside increases as well as the concentration of individual polyglycosides to the total, i.e. DP2 and DP3 fractions in relation to the sum of all DP fractions. Such compositions are disclosed in U.S. Pat. No. 5,266,690, the entire contents of which are incorporated herein by reference.

In its broadest embodiment, the process according to the invention comprises a haze elimination step in which the pH of a hydrogen peroxide-free aqueous solution of a glycoside product is adjusted to a value of from 3 to 8 with an aqueous acid solution such as sulfuric acid, hydrochloric acid, or phosphoric acid and the like. A hydrogen peroxide-free solution is defined as a solution in which no hydrogen peroxide is detectable by means of a sodium thiosulfate titration method as described in Example 5. The pH of the solution is maintained in the range of from 3 to 8 until the haze is essentially eliminated from the solution as determined by absence of a precipitate after centrifugation or where the absorbance of 50–70% by weight aqueous solution at 600 nm is less than 0.02. The haze elimination step can be carried out at any temperature in the range of from about room temperature or 70° F. to about 210° F. Preferably, the haze elimination step is carried out at a temperature of from 130° F. to 170° F. After the haze has been eliminated, the pH of the solution is raised to about 10 with an aqueous solution of a base such as aqueous sodium hydroxide followed by the addition of a sodium borohydride solution. The sodium borohydride is allowed to remain in contact with the glycoside product solution at a temperature of from about 110° F. to about 160° F. until the borohydride concentration is substantially zero as determined by differential headspace gas chromatography the details of which are set forth in Example 4.

In a preferred embodiment of the process according to the invention, an aqueous glycoside product stream containing from about 50% to about 70% of the glycoside product, free of hydrogen peroxide as determined by the sodium thiosulfate titrimetric method as set forth in Example 5, and having a pH of from about 10 to about 11 is introduced into a stirred tank reactor. A solution containing at least 10% by weight sulfuric acid is then added to the reactor until the pH of the solution containing the glycoside product is from about 4 to about 7. The temperature is then held from about 145° F. to about 170° F. The pH and temperature are maintained until the absorbance of 50–70% by weight aqueous solution at 600 nm is less than 0.02. After the haze has been substantially eliminated, the temperature of the glycoside product solution is adjusted to from about 140° F. to about 150° F. and the pH is then raised to from about 9 to about 10 by addition of an aqueous solution containing from about 30% to about 60% by weight of sodium hydroxide. An aqueous solution of sodium borohydride containing from about 10% to about 15% by weight of sodium borohydride and from about 30% to about 40% by weight of sodium hydroxide is then added to the glycoside product solution so that the solution contains from about 0.01% to about 0.2% by weight of sodium borohydride based on glycoside product. The resulting pH after the sodium borohydride addition will typically be from about 11.2 to about 11.5. The reaction temperature is maintained until the concentration of the sodium borohydride is substantially zero as determined by differential headspace gas chromatography. The following examples are meant to illustrate but not limit the invention.

EXAMPLE 1

About 148 grams of a peroxide bleached, aqueous alkyl polyglycoside at about 54% active glycoside had a pH=9.98 and no residual $H_2O_2$ as determined by the sodium thiosulfate titrimetric method (Example 5) were placed in a flask. The absorbance at ambient temperature at 470 nm was 0.132 (at as is pH) and the absorbance at 600 nm was 0.053 (at as is pH). The sample was hazy and a precipitate formed on centrifugation. The sample was warmed to 160° F. and titrated with 1.694 g, 20 wt % aqueous sulfuric acid to pH 6.7. The sample was stirred at 160° F. and then cooled to 140° F. and held there until the absorbance at 600 nm was <0.02 and a centrifuged sample was clear and free of precipitate. The absorbance at 470 nm was 0.092 and at 600 nm it was 0.020. A sample was titrated with 0.52 g of a 50 wt % aqueous caustic solution to a pH of 10.2. Residual carbohydrate reduction was commenced with the introduction of 0.1%, alkyl glycoside basis, of sodium borohydride as a 12% active solution in 14 molar sodium hydroxide. The sodium borohydride was allowed to remain in contact with the glycoside product solution at a temperature of from about 140° F. to about 150° F. until the borohydride concentration was substantially zero as determined by differential headspace gas chromatography.

EXAMPLE 2

About 148,700 pounds of an aqueous, peroxide bleached, alkyl polyglycoside at about 54% active glycoside had a pH=9.98 and no residual $H_2O_2$ as determined by the sodium thiosulfate titrimetric method (Example 5) were placed in a stirred tank reactor. The absorbance at ambient temperature at 470 nm was 0.132 (at as is pH) and the absorbance at 600 nm was 0.053 (at as is pH). The sample was hazy and a precipitate formed on centrifugation. The sample was warmed to 160° F. and titrated with 364 pounds of a 93 wt % aqueous sulfuric acid which was mixed with 1330 pounds of softened water, prior to introduction into the product, over a 70 minute period to a pH of 6.7. The sample was agitated and cooled to 140° F. and held there until the absorbance at 600 nm was <0.02 and a centrifuged sample was clear and free of precipitate. The absorbance at 470 nm was 0.092 and at 600 nm it was 0.020. A sample was titrated with 520 pounds of a 50 wt % aqueous caustic solution to a pH of 10.2. Residual carbohydrate reduction was commenced with the introduction of 0.1%, alkyl glycoside basis, of sodium borohydride as a 12% active solution in 14 molar sodium hydroxide. The sodium borohydride was allowed to remain in contact with the glycoside product solution at a temperature of from about 140° F. to about 150° F. until the borohydride concentration was substantially zero as determined by differential headspace gas chromatography.

EXAMPLE 3

Spectrophotometric Haze Measurement

A 13×100 mm Dispo Culture Tube (VWR Products Catalog #60825-571 or equivalent) was filled about half way with a sample of product from a typical alkyl polyglycoside reaction after the bleaching step. The pH of the sample was adjusted to 7 by adding a small amount of a 30% wt/wt aqueous sulfuric acid solution. The Spectronic 20 was calibrated to read 0.0 absorbance using a deionized water blank at 600 nm. The absorbance of the sample was taken as the average of four readings with each reading taken after a 35° rotation of the sample tube. The absorbance was less than 0.02.

EXAMPLE 4

Differential Headspace Gas Chromatography

A liquid sample of the reaction mixture was withdrawn from the reactor after about 3.5 hours following the borohydride addition. Into a first 60 ml capacity headspace vial (Alltech Cat. No. 66101) were placed 5 grams of sample from the reactor which had been centrifuged to be free of air bubbles and 10 grams of ethylene glycol. Into a second 60 ml capacity headspace vial were placed 5 grams of sample from the reactor which had been centrifuged to be free of air bubbles, 10 grams of ethylene glycol, and 0.5 grams of 30% wt/wt aqueous sulfuric acid. After weighing, both vials were sealed with a septum and aluminum seal and crimped immediately. The contents of both vials were mixed by swirling the vials on a flat surface so as not to introduce bubbles. The vials were then placed in an oven at 150° F. for 5 minutes and the vials were again swirled to mix until all striations were eliminated. A gas tight syringe was flushed 3 times with air before insertion into the headspace of each vial. About 3 ml of gas was withdrawn from the headspace of each vial allowing 5 seconds for the gas to fill the syringe barrel. The valve on the syringe was then closed and the gas inside it was compressed to 1 ml and pressure released for 3 sec just before injecting 1 ml of the gas into the gas chromatograph. The headspace gas from both samples were injected and the % $H_2$ was calculated according the following formula (hydrogen RF is calculated below):

$$\% \; H_2 \; \text{in Sample} = \frac{\text{Peak area of H2/mls sample injected}}{\text{Hydrogen } RF}$$

The gas chromatograph was calibrated with a gas mixture comprised of 1.00% vol/vol hydrogen in nitrogen according to the following procedure. About a 3' length of tygon tubing was attached to the calibration gas regulator valve which was set at approximately 5 psi. The tubing was pierced with the needle of the gas syringe and then flush several times with calibration gas prior to withdrawing 3 mls of gas. The syringe valve was closed and the gas was withdrawn from the tubing. The gas in the syringe was compressed to 2 mls prior to expelling 1 ml of gas, waiting 3 seconds, and then injecting the 1 ml into the GC. The hydrogen peak area was recorded. The procedure was carried a total of 3 times and the results were averaged. The average peak area is used to calculate hydrogen RF according to the following formula:

$$\text{Hydrogen } RF = \frac{\text{Average peak area obtained for hydrogen}}{\text{Certified \% hydrogen of calibration gas}}$$

Chromatographic Conditions: Hewlett-Packard 5890 Series II or similar, equipped with a TC detector and a Spectra Physics 4400 or similar integrator/chart terminal. Gas tight syringe: 5 mL Unimetric #7005GLL. Alltech No. 170051 Syringe needles: 2" long, KEL-F hub, point style #5, Alltech No. 90422 Luer Lock shut off valve for syringe G.C. Column: 6'×⅛" S.S. packed with washed 80/100 mesh Mole Sieve 5A. Altech No. 5605 PC. (Before use, the column must be conditioned at 300° C. for 10 hours with nitrogen flow through the column)

| Detector Temperature: | 150.° C. |
| --- | --- |
| Injection Port Temperature | 50.° C. |
| Oven Program (isothermal): | |
| Initial Temperature | 30.° C. |
| Initial Time | 4 Min |
| Initial Rate | 0.° C./min |
| Gas Flows: | |
| Carrier Gas (Nitrogen) | 10. mls/min. |
| Reference | 10. mls/min. |
| Detector Attenuation | 1. |
| Detector Range: | 2. |
| Detector Sensitivity: | Low |
| TCD Gas Selection: | $N_2$ |
| Injection Volume: | 1.0 ml |

EXAMPLE 5

Hydrogen Peroxide Titration Method

Into a 250 ml beaker were placed about 80–100 ml of $H_2O_2$ titration solvent and 1–1.5 grams (to the nearest 0.0001 grams) of APG ® from the $H_2O_2$ bleaching reactor. The $H_2O_2$ titration solvent is comprised of 300 ml of glacial acetic acid in 3000 ml of deionized water. While stirring the contents of the beaker about 2–3 drops of a 20% aqueous slurry of ammonium molybdate were added and the color of the solution was noted. After all of the APG ® had dissolved, about 1 gram of solid potassium iodide was added and a yellow-to-orange color developed. The solution was then quickly titrated with 0.1N aqueous sodium thiosulfate solution to an end point which is the same color as the color noted before the addition of the KI. The final end point color held for 60 seconds. The amount of $H_2O_2$ in the APG ® was calculated according to the following equation: ppm $H_2O_2$ =ml of sodium thiosulfate ×340/grams of sample.

What is claimed is:

1. A process for improving the color of a glycoside product comprising the steps of: (1) providing a hydrogen peroxide-free aqueous solution of a peroxide-bleached glycoside product; (2) adjusting and maintaining the pH of said solution to a range of from about 3 to about 8 for a time sufficient to substantially eliminate haze; (3) raising the pH of said solution to from about 9 to about 11; (4) contacting the solution from step (3) with a color stabilizing amount of from about 0.01 to about 0.2 weight percent, on a glycoside product dry weight basis, with a Group I or Group II metal borohydride to substantially reduce the propensity of said glycoside product to darken upon exposure to elevated temperatures under alkaline conditions and to exhibit a haze at a pH of about 7.

2. The process of claim 1 wherein the pH in step (2) is from about 6.5 to about 7.

3. The process of claim 1 wherein said metal borohydride is sodium borohydride.

4. The process of claim 1 wherein said glycoside product is a compound of the formula I:

$$RO(R'O)_y(G)_n \qquad (I)$$

wherein R is a monovalent organic radical containing from about one to about 30 carbon atoms; R' is a divalent hydrocarbon radical containing from 2 to about 4 carbon atoms; y is a number having an average value of from 0 to about 12; n is a number from 1 to 3 and G is a moiety derived from a reducing saccharide containing 5 or 6 carbon atoms.

5. The process of claim 4 wherein R is a monovalent, saturated aliphatic group which contain from 1 to about 18 carbon atoms; y is zero; n is a number from 1 to 3.

6. The process of claim 1 wherein said glycoside product is a composition which is comprised of mixtures of compounds of formula I:

$$RO(R'O)_y(G)_n \qquad (I)$$

wherein y is zero; n is a number from 1 to 3; G is a moiety derived from a reducing saccharide containing 5 or 6 carbon atoms; and R is an alkyl radical having from 6 to 18 carbon atoms in which the average carbon chain length of the alkyl groups of the compounds of formula I in the composition is from about 9 to about 14 and wherein said composition is comprised of a mixture of two or more of at least binary components of alkylpolyglycosides wherein each binary component is present in the mixture in relation to its average carbon chain length in an amount effective to provide the surfactant composition with the average carbon chain length of about 9 to about 14 and wherein at least one, or both binary components, comprise a Flory distribution of polyglycosides derived from an acid-catalyzed reaction of an alcohol containing 6–20 carbon atoms and a suitable saccharide from which excess alcohol has been separated.

7. The process of claim 1 wherein said glycoside product is a composition which is comprised of mixtures of compounds of formula I:

$$RO(R'O)_y(G)_n \qquad (I)$$

wherein y is zero; n is a number from 1.8 to 3; R is an alkyl radical having from 8 to 20 carbon atoms; and G is a moiety derived from a reducing saccharide containing 5 or 6 carbon atoms; and wherein said composition has an HLB in the range of about 10 to about 16 and a non-Flory distribution of glycosides comprised of a mixture of an alkyl monoglycoside and a mixture of alkyl polyglycosides having varying degrees of polymerization of 2 and higher in progressively decreasing amounts, in which the amount by weight of polyglycoside having a degree of polymerization of 2, or mixtures thereof with the polyglycoside having a degree of polymerization of 3, predominate in relation to the amount of monoglycoside, said composition having an average degree of polymerization of about 1.8 to about 3.

8. A process for improving the color of a glycoside product comprising the steps of: (1) providing a hydrogen peroxide-free aqueous solution of a peroxide-bleached glycoside product; (2) adjusting the pH of said solution to a range of from about 4 to about 7; (3) adjusting and maintaining the temperature of said solution to from about 70° F. to about 170° F. for a time sufficient to substantially eliminate haze; (4) raising the pH of the solution to from about 9.5 to about 10.5; (5) contacting the solution from step (4) with a color stabilizing amount of from about 0.01 to about 1 weight percent, on a glycoside product dry weight basis, of a Group I or Group II metal borohydride to substantially reduce the propensity of said glycoside product to darken upon exposure to elevated temperatures under alkaline conditions and to exhibit a haze at a pH of about 7.

9. The process of claim 8 wherein said temperature in step (3) is from about 150° F. to about 170° F.

10. The process of claim 8 wherein said metal borohydride is sodium borohydride.

11. The process of claim 8 wherein said glycoside product is a compound of the formula I:

$$RO(R'O)_y(G)_n \qquad (I)$$

wherein R is a monovalent organic radical containing from about one to about 30 carbon atoms; R' is a divalent hydrocarbon radical containing from 2 to about 4 carbon atoms; y is a number having an average value of from 0 to about 12; n is a number from 1 to 3; and G is a moiety derived from a reducing saccharide containing 5 or 6 carbon atoms.

12. The process of claim 11 wherein R is a monovalent, saturated aliphatic group which contain from 1 to about 18 carbon atoms; y is zero; n is a number from 1 to 3.

13. The process of claim 8 wherein said glycoside product is a composition which is comprised of mixtures of compounds of formula I:

$$RO(R'O)_y(G)_n \qquad (I)$$

wherein y is zero; x is a number from 1 to 3; G is a moiety derived from a reducing saccharide containing 5 or 6 carbon atoms; and R is an alkyl radical having from 6 to 18 carbon atoms in which the average carbon chain length of the alkyl groups of the compounds of formula I in the composition is from about 9 to about 14 and wherein said composition is comprised of a mixture of two or more of at least binary components of alkylpolyglycosides wherein each binary component is present in the mixture in relation to its average carbon chain length in an amount effective to provide the surfactant composition with the average carbon chain length of about 9 to about 14 and wherein at least one, or both binary components, comprise a Flory distribution of polyglycosides derived from an acid-catalyzed reaction of an alcohol containing 6–20 carbon atoms and a suitable saccharide from which excess alcohol has been separated.

14. The process of claim 8 wherein said glycoside product is a composition which is comprised of mixtures of compounds of formula I:

$$RO(R'O)_y(G)_n \qquad (I)$$

wherein y is zero; x is a number from 1.8 to 3; R is an alkyl radical having from 8 to 20 carbon atoms; and G is a moiety derived from a reducing saccharide containing 5 or 6 carbon atoms; and wherein said composition has an HLB in the range of about 10 to about 16 and a non-Flory distribution of glycosides comprised of a mixture of an alkyl monoglycoside and a mixture of alkyl polyglycosides having varying degrees of polymerization of 2 and higher in progressively decreasing amounts, in which the amount by weight of polyglycoside having a degree of polymerization of 2, or mixtures thereof with the polyglycoside having a degree of polymerization of 3, predominate in relation to the amount of monoglycoside, said composition having an average degree of polymerization of about 1.8 to about 3.

* * * * *